United States Patent [19]

Butte, Jr. et al.

[11] 3,998,881

[45] Dec. 21, 1976

[54] HYDROGENATION OF PHTHALONITRILES USING RHODIUM CATALYST

[75] Inventors: Walter Albert Butte, Jr., West Chester; William J. Murtaugh, Eddystone, both of Pa.

[73] Assignee: Sun Ventures, Inc., St. Davids, Pa.

[22] Filed: Nov. 13, 1974

[21] Appl. No.: 523,298

[52] U.S. Cl. .................... 260/563 R; 252/477 Q
[51] Int. Cl.² .................................. C07C 85/02
[58] Field of Search .......... 252/477 Q; 260/563 D, 260/377, 563 R

[56] References Cited

UNITED STATES PATENTS

| | | | |
|---|---|---|---|
| 2,534,088 | 12/1950 | Webb | 260/563 R |
| 3,196,179 | 7/1965 | Robinson | 260/563 D |
| 3,372,195 | 3/1968 | Little | 260/563 D X |
| 3,673,251 | 6/1972 | Frampton et al. | 260/563 D |
| 3,739,009 | 6/1973 | Sturm et al. | 260/378 X |
| 3,880,928 | 4/1975 | Drake | 260/583 P |

FOREIGN PATENTS OR APPLICATIONS

| | | |
|---|---|---|
| 1,149,251 | 9/1966 | United Kingdom |
| 797,244 | 6/1958 | United Kingdom .......... 260/563 C |

OTHER PUBLICATIONS

Takagi et al. "Hydrogenation of Nitriles Catalyzed by Platinum Metals" in Sci. Pap. Inst. Phys. Chem. Res. (Tokyo), 61(3), 114–117, 1967.

*Primary Examiner*—Allen B. Curtis
*Attorney, Agent, or Firm*—J. Edward Hess; Donald R. Johnson; Paul Lipsitz

[57] ABSTRACT

A process for the preparation of 1,3 or 1,4-bis(aminomethyl)cyclohexane by hydrogenating a solvent solution of iso- or terephthalonitrile at a temperature between about 50° and about 150° C., at a pressure of between about 500 and about 1500 psig., and in the presence of a supported rhodium catalyst.

5 Claims, No Drawings

HYDROGENATION OF PHTHALONITRILES USING RHODIUM CATALYST

Aromatic dinitriles such as the phthalonitriles can be hydrogenated to phenylalkylamines with skeletal nickel and cobalt catalysts, but hydrogenation of the aromatic ring does not occur under the conditions ordinarily employed. Further hydrogenation of the ring structure of phenylalkylamines is difficult presumably because of the known inhibiting effect that strong nitrogen bases exert upon common catalyst systems. Thus, hydrogenation of phenyl alkylamines with Raney nickel requires very severe conditions of temperature and pressure and extensive deamination is encountered (M. Metayer, Bull. Soc. Chim. France, 1952, 276). Platinum catalysts can be used under acidic conditions but the product is transformed to a salt which must be neutralized in order to isolate the free base (B. L. Zenite, et. al. J. Am. Chem. Soc 69, 1117, 1947). U.S. Pat. No. 3,117,162 discloses that rhodium may be used to hydrogenate propionitrile with various solvents, and it was observed that in solvent systems good yield of primary amine could not be obtained. Also, some solvents such as dioxane, chloroform, carbon tetrachloride, etc. poisoned the catalyst. The same patent also discloses use of a rhodium catalyst and a hexane solvent to hydrogenate benzonitrile, but no ring hydrogenation was observed.

It has now been found that meta- or terephthalonitrile may be efficiently hydrogenated to effect reduction of not only the cyanoalkyl groups, but also the aromatic ring. Thus, the process of the invention enables isophthalonitrile or terephthalonitrile to be converted to the corresponding bis(aminomethyl)cyclohexane in good yield by a single step hydrogenation technique. In accord with the invention meta- or terephthalonitrile is catalytically hydrogenated at a temperature between about 50°C. and about 150°C., at a pressure of from about 500 to about 1500 psig. using a supported rhodium catalyst and carrying out the hydrogenation in an inert organic solvent having a solubility parameter of from about 9 to about 12.

Preferably, the process will be carried out with terephthalonitrile to give 1,4-diaminomethylcyclohexane, but, as indicated, the corresponding diaminomethylcyclohexane from isophthalonitrile may also be obtained by the process of the invention.

As indicated, the process will be carried out in an inert solvent system where the solvent is inert to hydrogenation and has a solubility parameter of from about 9 to 12. The concept of solubility parameter (abbreviated herein as "S.P.") is well understood in the art and is described in detail in Ind. and Eng. Chemistry, Prod. Res. and Dev. Section, Vol. 8, No. 1, Mar. 19, 1969, pages 2–11, and in the Kirk-Othmer Encyclopedia of Chemical Technology, Volume 18, pages 566 to 569. Thus, for example, preferred suitable solvents will include saturated aliphatic ethers and alcohols such as tetrahydrofuran (S.P. =9.4), dimethyldiethylene glycol (S.P. = 9.4), dioxane (S.P. = 10.01), 2-ethylhexanol (S.P. = 9.7), chloroform (S.P.=9.2), n-butanol (S.P. = 11.3), and the like. Although benzene has an S. P. of 9.02 it is not suitable because it is not inert, due to the hydrogenation of the ring which will occur. However, it is also to be understood that in accord with known prior art techniques, the solvent power may be adjusted by mixing with an appropriate amount, usually about 10 to about 25 volume percent, of anhydrous ammonia. This technique is useful for at least two purposes:

1. to increase the solubility parameter of the solvent system to the preferred value of about 11 and,
2. to reduce the amount of secondary amine by-products formed which tend to poison the catalyst. Thus, it is preferred to operate the process by using ammonia in the solvent system.

The amount of solvent used is not critical, but it is desirable to use enough to readily dissolve the nitrile at the reaction temperature. Usually, from 75 to 95 percent by volume of the reaction mixture is adequate. Larger amounts may be employed, but there is no particular benefit in doing so.

Reaction conditions will be at a temperature of from about 50° to about 150° C. and at a pressure of between about 500 and about 1500 psig. These conditions are relatively mild and thereby provide another important advantage for the process since lower operating costs result from use of mild conditions. It is also particularly surprising that hydrogenation of the aromatic ring can be made to occur under these relatively mild conditions. Preferred temperature for the process will be about 100° C. and preferred pressure is about 1000 psi.

The catalyst, as indicated, will be supported rhodium. Preferably, the supports useful will include carbon, alumina and activated alumina, silica, including synthetic gel and kieselguhr, calcium carbonate, titanium dioxide, bentonite, barium sulfate, etc. Preferably, the rhodium catalyst (employed in the form of its black) will be from about 0.1 to 10 percent by weight of the total catalyst and support. These catalysts and their method of preparation are known in the art (see for example U.S. Pat. No. 3,117,162).

In carrying out the process of the invention the aromatic dinitrile, solvent, and catalyst are charged to the appropriate pressure reactor and after closing the reactor ammonia is added and it is heated up to about 100° to about 150° C. At this point hydrogen is pressured in to the desired pressure and as stirring or other agitation is maintained the uptake of hydrogen is observed. After hydrogen absorption stops, stirring is continued for a short time, the reactor cooled, opened and the contents filtered. The filtrate is distilled to separate solvent from the product. Isolation and purification of the product is readily accomplished by vacuum distillation.

It will be understood, of course, that in addition to carrying out the process by the batch technique described above, a continuous operation may also be used. In such a case, a packed bed of catalyst may be used through which the reaction solution and hydrogen are simultaneously passed.

In order to further illustrate the invention the following examples are given:

EXAMPLE I

Terephthalonitrile (40 g.), 800 ml. dioxane, 36 g. of a 5% rhodium on alumina catalyst and 200 ml. liquid ammonia was charged to a 2 liter stirred autoclave. The reactor was heated to 100° C. with a resulting pressure rise to 340 psi. Hydrogen was then introduced at 1000 psi. and it was noted that the hydrogen was rapidly absorbed for a period of about 35 min. Stirring was continued for an additional 85 min. at 1000 psi. and 100° C. and then the reactor was cooled and vented. The reactor contents were removed and filtered to recover the catalyst. NMR analysis of the filtrate showed that the aromatic ring had been largely hydrogenated to a cycloaliphatic. The solvent was recovered by distillation and the residual oil was vacuum distilled to give 29.6 g. oil boiling 64°–74° C. at 0.2 mm. collected in two fractions. NMR analysis showed both fractions to be largely cycloaliphatic. The equivalent weight of the higher boiling fraction as determined by titration with dilute hydrochloric acid was 71.6. The theoretical value for 1,4-bis-(aminomethyl)cyclohexane is 71.1, thus confirming the identity of the product.

EXAMPLE II

The catalyst recovered from the previous experiment was washed with dioxane and reused in another run which was identical except that the temperature and pressure were 150° C. and 1500 psig, respectively. After filtration and distillation, NMR analysis of the reaction product showed that the aromatic ring had been extensively hydrogenated and that none of the terephthalonitrile remained.

EXAMPLE III

Following the details of the above Example I, when terephthalonitrile was reduced over a 60 minute period using 6.0 g. of the supported rhodium catalyst, 1,4-bisaminomethlycyclohexane was obtained and 100% conversion of terephthalonitrile had occurred.

EXAMPLE IV

Isophthalonitrile (20 g.), 400 ml. dioxane and 18 g. of a 5% rhodium on alumina catalyst was charged to a 1 liter stirred autoclave. Nitrogen was used to purge air from the autoclave and then 100 ml. anhydrous ammonia was added. The autoclave was heated to 148° C. and then hydrogen was introduced at a pressure of 1500 psig. A rapid exotherm was noted accompanied by rapid uptake of hydrogen. After 10 min. the hydrogen consumption had nearly stopped and after 15 min. the reactor was rapidly cooled to about 40° C. Excess gas was allowed to vent and the reaction mixture was removed and filtered to remove the catalyst. The solution was concentrated at reduced pressure and vacuum distilled. A fraction boiling at 55° C (0.25 mm. Hg) that weighed 7.0 g. was collected. The equivalent weight of this fraction as determined by titration with dilute hydrochloric acid was 70.3. The theoretical value for 1,3-bis(aminomethyl)cyclohexane is 71.1 thus confirming the identity of the product.

EXAMPLE V

Terephthalonitrile (20 g.), 400 ml. dioxane and 18 g. of a 5% rhodium on alumina catalyst were placed in a 1 liter stirred autoclave. After purging with nitrogen, the autoclave was heated to 98° C and then hydrogen was introduced at 1000 psig. An exothermic reaction ensued causing the temperature to rise to 112° C. After 50 min. no further consumption of hydrogen was noted. Stirring was continued for 10 minutes more. Then, the reactor was cooled rapidly and vented. The product was filtered free of catalyst and distilled to give 6.1 g. of oil boiling about 53° C at .15 mm. Hg. with an equivalent weight of 85.7 indication that the 1,4-bis-(aminomethyl)cyclohexane was less pure than where ammonia was used in the solvent system.

EXAMPLE VI

Isophthalonitrile (20 g.), 400 ml. dioxane, 18 g. 5% rhodium on alumina catalyst were placed in a 1 liter stirred autoclave. The vessel was purged with nitrogen and then 100 ml. liquid ammonia was introduced. The reaction vessel was stirred and heated to 98° C. Internal pressure reached 320 psi. Hydrogen was admitted until the pressure reached 1000 psi. The temperature and pressure was regulated at 100° C and 1000 psi. for a period of 50 min. The reactor was then cooled and vented and the contents were removed and filtered. Upon distillation, the filtrate provided 11.9 g. of a fraction boiling at 60° C (0.2 mm. Hg). NMR analysis showed that the aromatic ring had been hydrogenated to a completely saturated ring.

The invention claimed is:
1. A process for the preparation of 1,3- or 1,4-bis-(aminomethyl) cyclohexane by hydrogenating in the presence of a supported rhodium catalyst at a temperature between about 50° and 150° C., and at a pressure between about 500 and about 1500 psig. a solution of iso- or terephthalonitrile in a solvent inert to said hydrogenation and having a solubility parameter of from about 9 to about 12 and said solution containing from about 10 to about 25 percent by volume of anhydrous ammonia.
2. The process of claim 1 where 1,3-bis-(aminomethyl) cyclohexane is prepared from isophthalonitrile.
3. The process of claim 2 where the solvent is dioxane.
4. The process of claim 1 where 1,4-bis-(aminomethyl) cyclohexane is prepared from terephthalonitrile.
5. The process of claim 4 where the solvent is dioxane.

* * * * *